(12) United States Patent
Ochi (10) Patent No.: US 11,291,389 B2
(45) Date of Patent: Apr. 5, 2022

(54) SENSOR INSERTION DEVICE

(71) Applicant: PHC Holdings Corporation, Tokyo (JP)

(72) Inventor: Takashi Ochi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

(21) Appl. No.: 16/962,119

(22) PCT Filed: Jan. 25, 2019

(86) PCT No.: PCT/JP2019/002499
§ 371 (c)(1),
(2) Date: Jul. 14, 2020

(87) PCT Pub. No.: WO2019/176324
PCT Pub. Date: Sep. 19, 2019

(65) Prior Publication Data
US 2020/0405201 A1 Dec. 31, 2020

(30) Foreign Application Priority Data
Mar. 13, 2018 (JP) .............................. JP2018-044839

(51) Int. Cl.
*A61B 5/145* (2006.01)
*A61B 5/00* (2006.01)
*A61B 90/00* (2016.01)

(52) U.S. Cl.
CPC ...... *A61B 5/14503* (2013.01); *A61B 5/14532* (2013.01); *A61B 5/6848* (2013.01); *A61B 90/03* (2016.02); *A61B 2090/034* (2016.02)

(58) Field of Classification Search
CPC ............ A61B 5/14532; A61B 5/14546; A61B 5/14503; A61B 2560/063; A61B 5/1451;
(Continued)

(56) References Cited

U.S. PATENT DOCUMENTS 8,979,800 B2 * 3/2015 Liniger ................. A61M 5/158
604/157
9,402,570 B2 8/2016 Pace et al.
(Continued)

FOREIGN PATENT DOCUMENTS

CN 106037763 10/2016
JP 2012-521822 9/2012
(Continued)

OTHER PUBLICATIONS

Extended European Search Report dated Apr. 8, 2021 in corresponding European Patent Application No. 19767152.2.
(Continued)

*Primary Examiner* — Eric F Winakur
*Assistant Examiner* — Alice Ling Zou
(74) *Attorney, Agent, or Firm* — Wenderoth, Lind & Ponack, L.L.P.

(57) ABSTRACT

A sensor insertion device comprises a sheath, a handle, an operating body provided in the handle, a carrier provided below the operating body, a guide needle unit holder that provided at the lower end of the carrier and detachably holds a guide needle that guides a sensor in the insertion direction, and an arm that is rotatably supported by the cylindrical portion of the sheath. The arm has an outer end portion disposed outside the sheath and an inner end portion disposed inside the sheath. The handle has an arm operation surface that abuts on the outer end portion of the arm. The carrier has a ceiling that abuts on the inner end portion of the arm.

11 Claims, 12 Drawing Sheets

(58) Field of Classification Search
CPC ............ A61B 5/14865; A61B 5/14735; A61B 5/1459; A61B 2560/06; A61B 5/157; A61B 5/15113; A61B 5/6848–6849; A61M 2005/1585; A61M 2230/201
See application file for complete search history.

(56) References Cited

U.S. PATENT DOCUMENTS

| | | | |
|---|---|---|---|
| 9,693,713 | B2 | 7/2017 | Pace et al. |
| 9,931,066 | B2 | 4/2018 | Pace et al. |
| 2006/0155316 | A1 | 7/2006 | Perez et al. |
| 2011/0082484 | A1* | 4/2011 | Saravia ................ A61B 5/0031 606/167 |
| 2011/0319729 | A1 | 12/2011 | Donnay et al. |
| 2012/0095406 | A1 | 4/2012 | Gyrn et al. |
| 2013/0150691 | A1 | 6/2013 | Pace et al. |
| 2015/0190076 | A1 | 7/2015 | Ohkoshi et al. |
| 2017/0042457 | A1 | 2/2017 | Pace et al. |
| 2017/0165451 | A1 | 6/2017 | Frey et al. |
| 2017/0188910 | A1 | 7/2017 | Halac et al. |
| 2017/0265791 | A1 | 9/2017 | Pace et al. |
| 2017/0290533 | A1* | 10/2017 | Antonio ................ A61M 5/158 |
| 2018/0317820 | A1 | 11/2018 | Pace et al. |

FOREIGN PATENT DOCUMENTS

| | | | |
|---|---|---|---|
| JP | 2013-523216 | 6/2013 | |
| JP | 2015-509011 | 3/2015 | |
| WO | WO-9933504 A1 * | 7/1999 | ............ A61M 5/158 |
| WO | 2014/045448 | 3/2014 | |

OTHER PUBLICATIONS

International Search Report dated Apr. 16, 2019 in International (PCT) Application No. PCT/JP2019/002499.

* cited by examiner

SENSOR INSERTION DEVICE

TECHNICAL FIELD

The present application relates to a sensor insertion device used to insert a sensor for measuring biological information into a patient's body in order to perform continuous blood glucose measurement, for example.

BACKGROUND ART

The configuration of a conventional sensor insertion device is as follows.

A conventional sensor insertion device comprises a cylindrical sheath having a lower end opening and an upper end opening; a cylindrical handle that slidably covers the outer peripheral surface of the sheath; an operating body that is provided in the handle; a carrier that is provided below the operating body; a guide needle holder that is provided at the lower end of the carrier and guides the sensor in the insertion direction; a holder for a biological information measurement device provided at the lower end of the carrier; a guide needle that can be moved in and out of the lower end opening of the sheath; and a spring that stores energy to slide the guide needle upward.

When this sensor insertion device is used to leave a sensor in a patient's arm, the patient presses the handle down after bringing the lower end opening of the sensor insertion device into contact with the upper arm. When the operating body of the handle causes the carrier to slide downward, the guide needle and the sensor of the biological information measurement device guided by the guide needle are inserted into the patient's arm. After that, the force of the spring is released, whereupon the guide needle is pulled out of the patient's upper arm.

As a result, the sensor of the biological information measurement device is left in the arm, and the installation of the biological information measurement device is complete (for example, Patent Literature 1 below).

CITATION LIST

Patent Literature

Patent Literature 1: Japanese Unexamined Patent Application Publication No. 2015-509011

SUMMARY

Technical Problem

A problem encountered with the prior art described above was that the patient sometimes experienced greater discomfort when the guide needle was withdrawn from the upper arm of the patient.

That is, in a conventional sensor insertion device, the guide needle is pulled out of the patient's upper arm by releasing the spring force, and the withdrawn guide needle hits a stopper and comes to a stop. At this point, the loud snap produced when the guide needle hits the stopper increases the discomfort (fear) of the patient.

Therefore, it is an object of the present invention to reduce discomfort on the part of the patient when using a sensor insertion device.

Solution to Problem

In order to achieve this object, the sensor insertion device of the present invention is a sensor insertion device for inserting a sensor for measuring biological information into a patient's body, comprising a cylindrical sheath having a lower end opening and an upper end opening; a cylindrical handle that slidably covers the outer peripheral surface of the sheath and that slides up and down in the axial direction of the cylindrical sheath; an operating body that is provided in the handle and moves up and down integrally with the handle; a carrier that is provided below the operating body; a guide needle holder that is provided at the lower end of the carrier, guides the sensor in the insertion direction, and detachably holds a guide needle that is inserted into the patient's body at a specific insertion position; and an arm that is supported rotatably around a rotation shaft fixed to the cylindrical sheath.

The arm has an outer end portion disposed on the outer peripheral surface side of the sheath, and an inner end portion disposed on the inner peripheral surface side of the sheath. The handle has an arm operation surface that abuts on the outer end portion of the arm. The carrier has an arm receiver that abuts on the inner end portion of the arm.

The present invention achieves its intended object through the above configuration.

Advantageous Effects

That is, in the present invention, the arm is rotatably supported by the cylindrical portion of the sheath. The arm has an outer end portion disposed on the outer peripheral surface side of the sheath and an inner end portion disposed on the inner peripheral surface side of the sheath. The handle is provided with an arm operation surface that abuts on the outer end portion of the arm, and the carrier is provided with an arm receiver that abuts on the inner end portion of the arm.

Therefore, when the patient pushes down on the handle when pulling out the guide needle from the upper arm of the patient, the arm operation surface of the handle pushes down the outer end portion of the arm. The arm then rotates, the inner end portion of the arm moves upward, and the carrier is pushed up via the arm receiver.

Consequently, the guide needle at the lower end portion of the carrier is pulled out of the patient's upper arm. That is, the guide needle is pulled out by the rotation of the arm. Therefore, since the guide needle is pulled out without the use of a spring, no snapping noise is produced by release of the stored energy of the spring.

As a result, the patient is subjected to less discomfort (fear).

DESCRIPTION OF EMBODIMENTS

An embodiment of the present invention will now be described in detail with reference to the drawings.

In the following embodiments, "upper" and "lower" mean "upper" and "lower" in the usage state (attached to the patient 2) of the sensor insertion device 1 (an example of a sensor insertion device) shown in FIG. 9, etc. That is, the side of the body on which the sensor insertion device 1 is attached to the patient 2 is referred to as "lower," and the opposite side is referred to as "upper."

Embodiment 1

Figure 1:
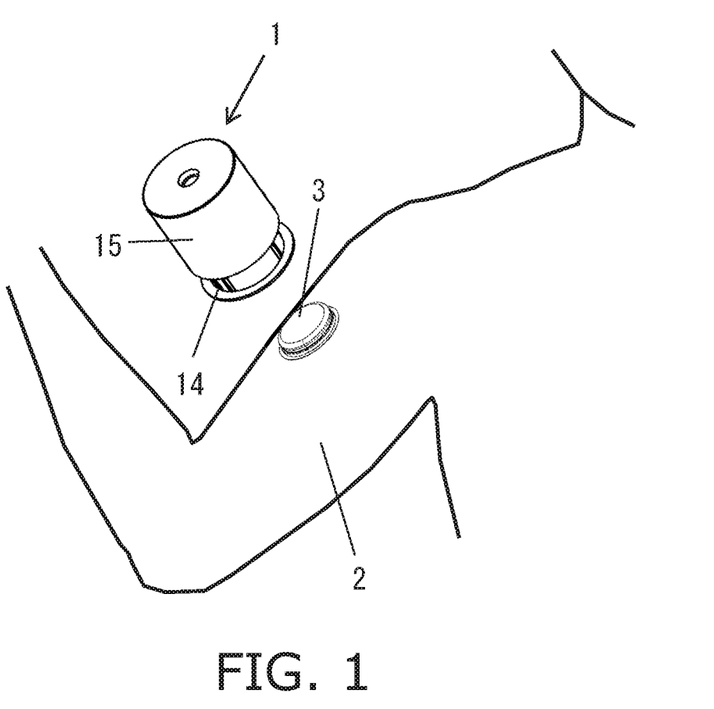
FIG. 1 is an oblique view of the sensor insertion device according to Embodiment 1 of the present invention, and a biological information measurement device attached using this sensor insertion device.

FIG. 1 shows a sensor insertion device 1 and a biological information measurement device 3 that is attached by the sensor insertion device 1 to the upper arm 2 of a patient. The biological information measurement device 3 is used to perform continuous blood glucose measurement, and measures the blood glucose level every 5 minutes, continuously for 1 to 2 weeks, for example. This allows the user to ascertain the tendency of the blood glucose state of the patient over a predetermined period, and the blood glucose state while asleep.

Figure 2:
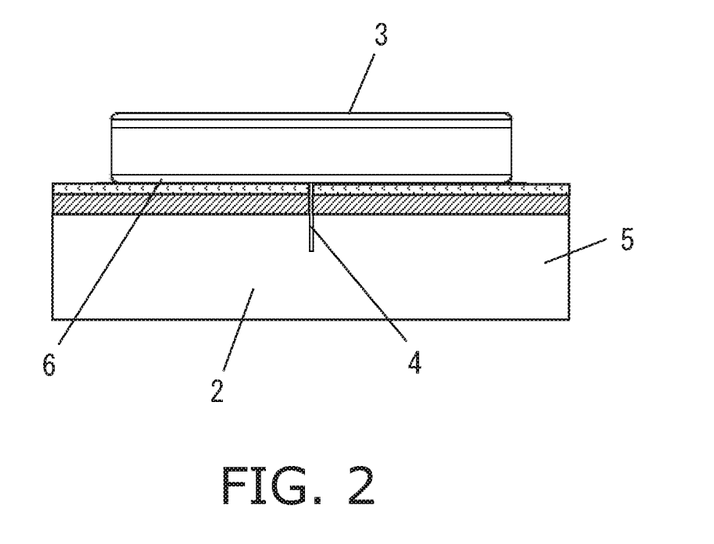
FIG. 2 is a diagram of the mounted state of the biological information measurement device in FIG. 1.

FIG. 2 is a diagram showing the attached state of the biological information measurement device 3 in FIG. 1.

A needle-shaped sensor 4 projects from the lower surface of the biological information measurement device 3. The sensor 4 is left in the upper arm 2 with its tip extending to the subcutaneous tissue 5. The sensor 4 is used to measure biological information, and measures the concentration of glucose (blood glucose level) in interstitial fluid, for example. The sensor 4 is inserted into the patient's body (such as into the upper arm 2) by the sensor insertion device 1.

Figure 3:
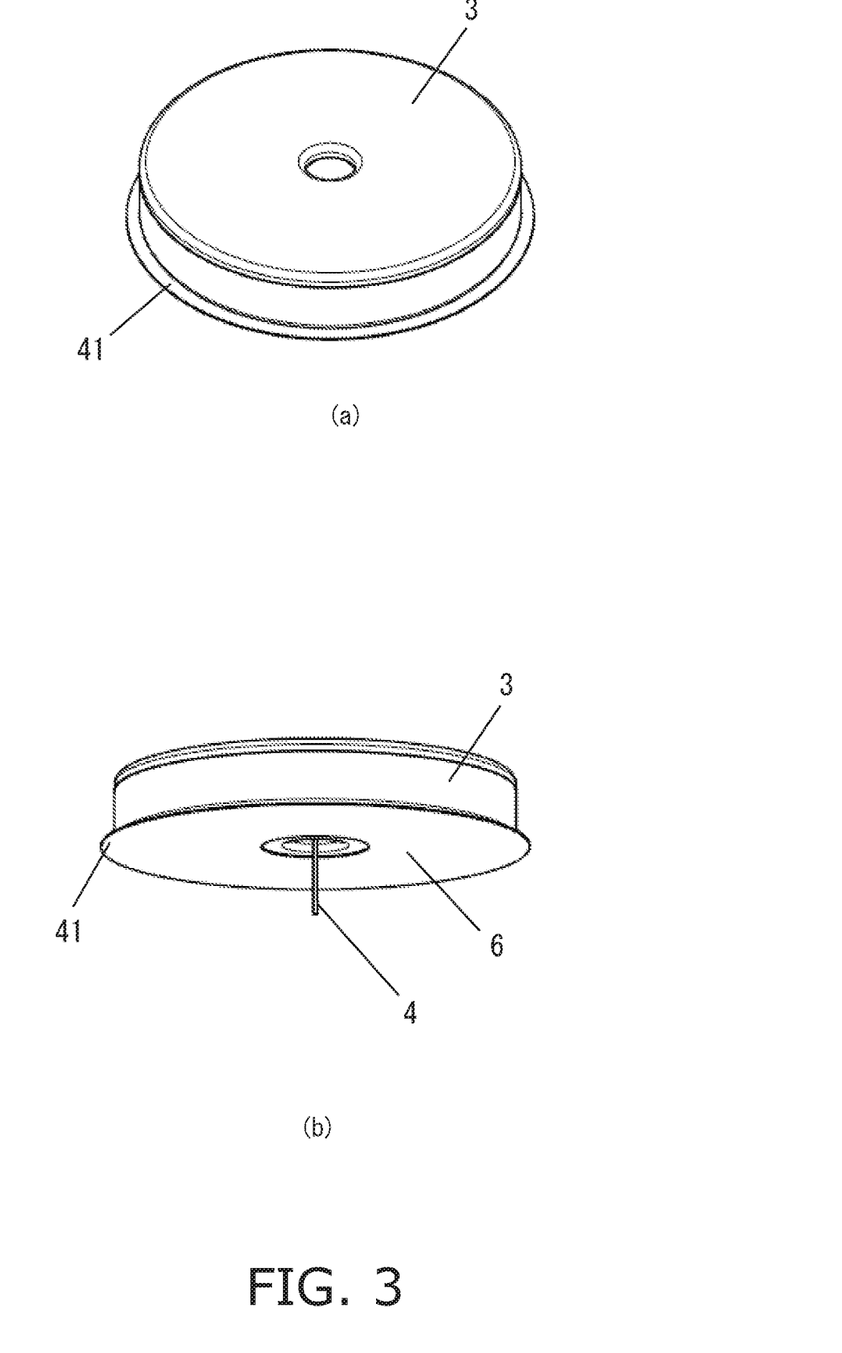
FIG. 3a is an oblique view of the biological information measurement device in FIG. 1 from above.
FIG. 3b is an oblique view of the biological information measurement device in FIG. 1 from below.

FIG. 3a is a diagram of the biological information measurement device 3 as seen from above. The biological information measurement device 3 is formed substantially in a disc shape. The lower surface of the biological information measurement device 3 is provided with an adhesive portion 6, as shown in FIG. 3b, so that it will stick well to the patient's skin.

Figure 4:
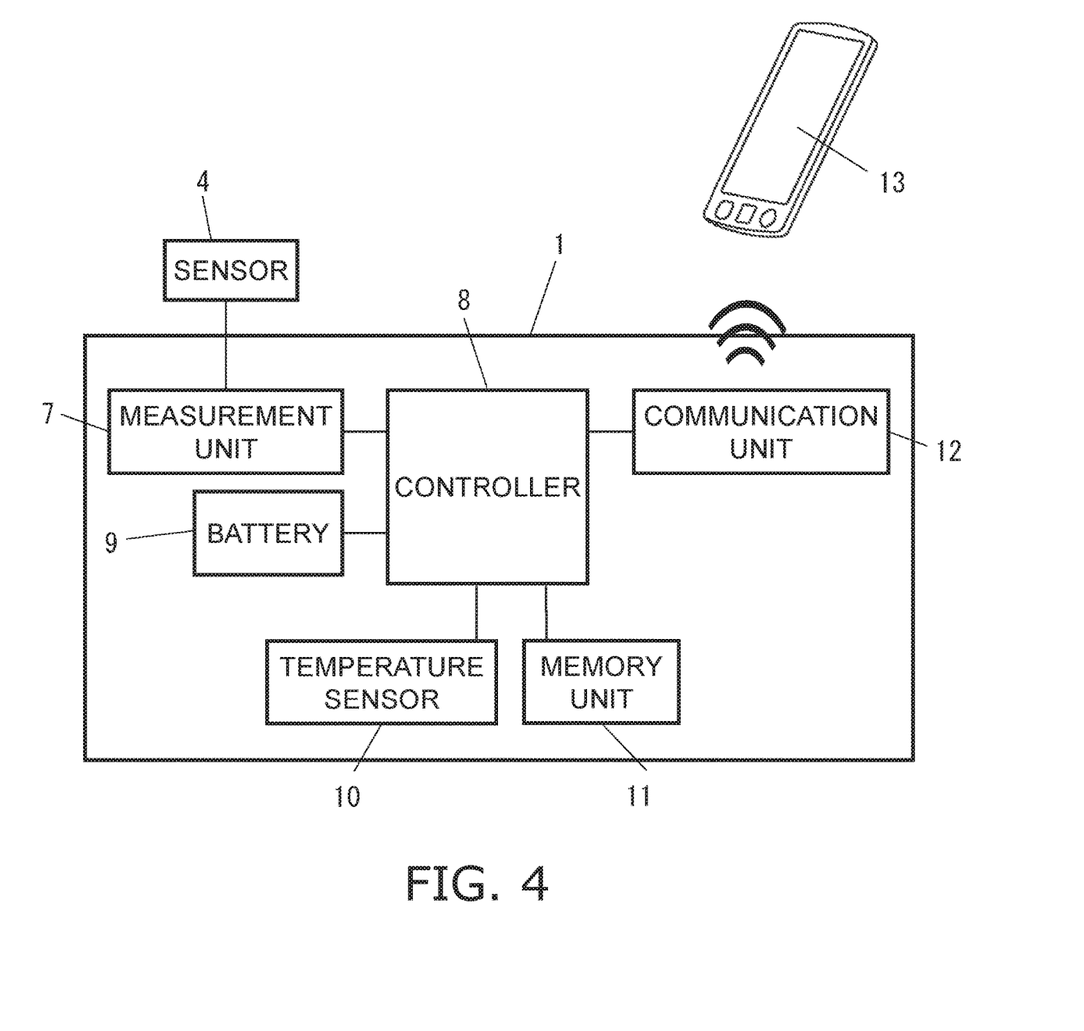
FIG. 4 is a control block diagram of the biological information measurement device in FIG. 1.

FIG. 4 is a control block diagram of the biological information measurement device 3.

The sensor 4 is connected to a measurement unit 7. The measurement unit 7 is connected to a controller 8. A battery 9, a temperature sensor 10, a memory unit 11, and a communication unit 12 are electrically connected to the controller 8.

With the biological information measurement device 3, the measurement unit 7 uses the sensor 4 to measure the blood glucose level at regular time intervals (such as every 5 minutes). The controller 8 corrects the blood glucose level on the basis of the temperature sensed by the temperature sensor 10, and then stores it in the memory unit 11. The controller 8 also transmits measurement values to an external device (such as a mobile phone 13) via the communication unit 12.

The biological information measurement device 3 is attached to the upper arm 2 by using the sensor insertion device 1 shown in FIG. 1.

This sensor insertion device 1 will be described in detail.

Figure 5:
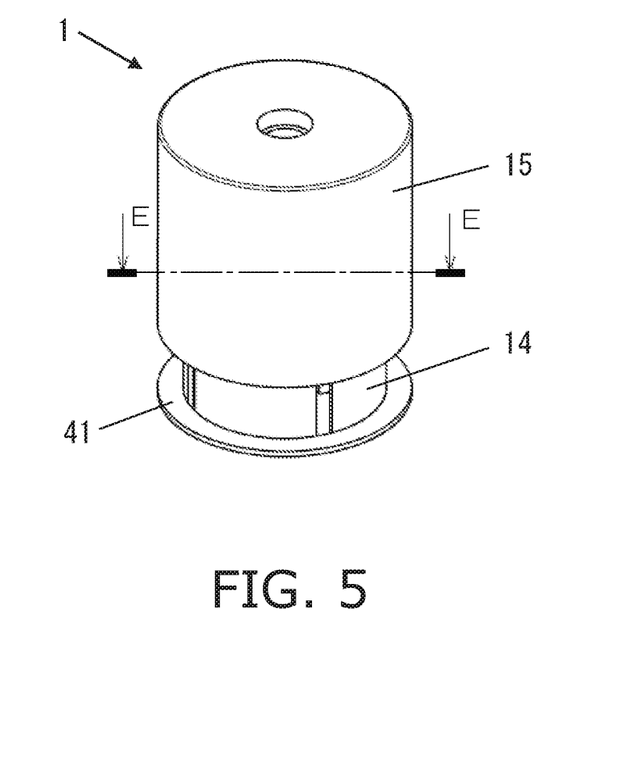
FIG. 5 is an oblique view of the sensor insertion device in FIG. 1.

FIG. 5 is an oblique view of the sensor insertion device 1.

The sensor insertion device 1 has a cylindrical sheath 14 and a cylindrical handle 15 that covers the outer peripheral surface of the sheath 14 and moves up and down along the outer peripheral surface.

Figure 6:
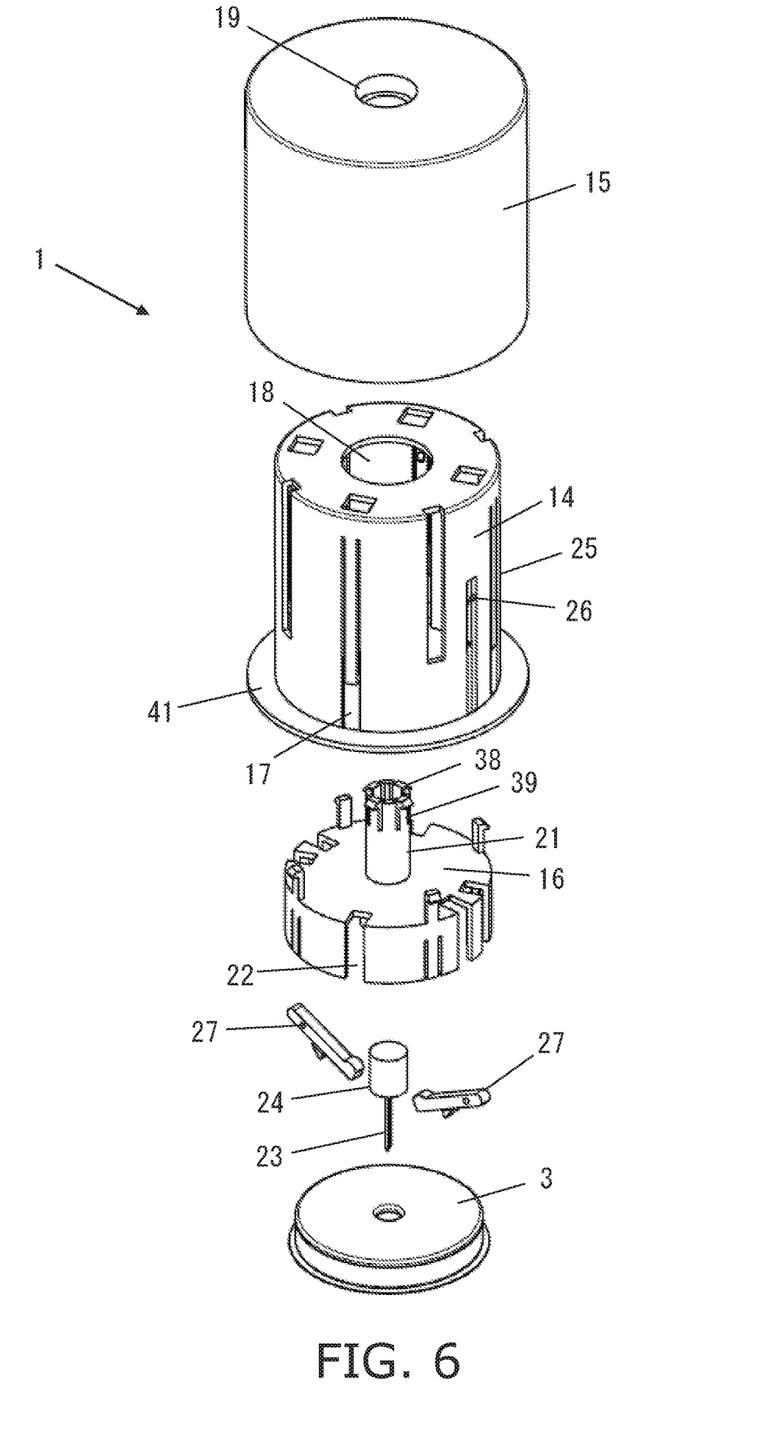
FIG. 6 is an exploded oblique view of the sensor insertion device in FIG. 1.

FIG. 6 is an exploded oblique view of the sensor insertion device 1.

The sensor insertion device 1 has a cylindrical carrier 16 that slides on the inner peripheral surface side of the sheath 14.

The sheath 14 has a lower end opening 17 provided at the lower end, and an upper end opening 18 provided in the center of the upper end.

The handle 15 slidably covers the outer peripheral surface of the sheath 14 from the upper end side. The handle 15 has an opening 19 in its upper surface. A cylindrical operating body 20 (see FIG. 9) is provided on the inner side of the opening 19. The operating body 20 is inserted into the sheath 14 through the upper end opening 18, and slides in and out of the upper end opening 18 of the sheath 14. The carrier 16 is disposed below the operating body 20 so as to be opposite thereto.

Figure 10:
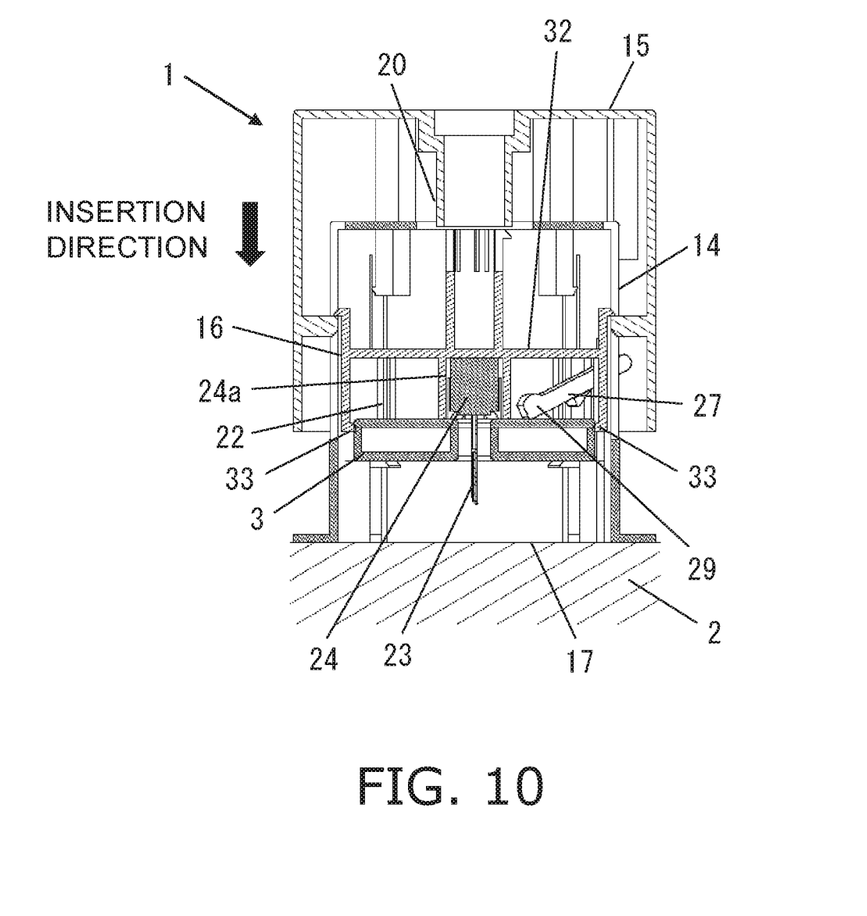
FIG. 10 is a cross section along the C-C line of the sensor insertion device in FIG. 8.
Figure 11:
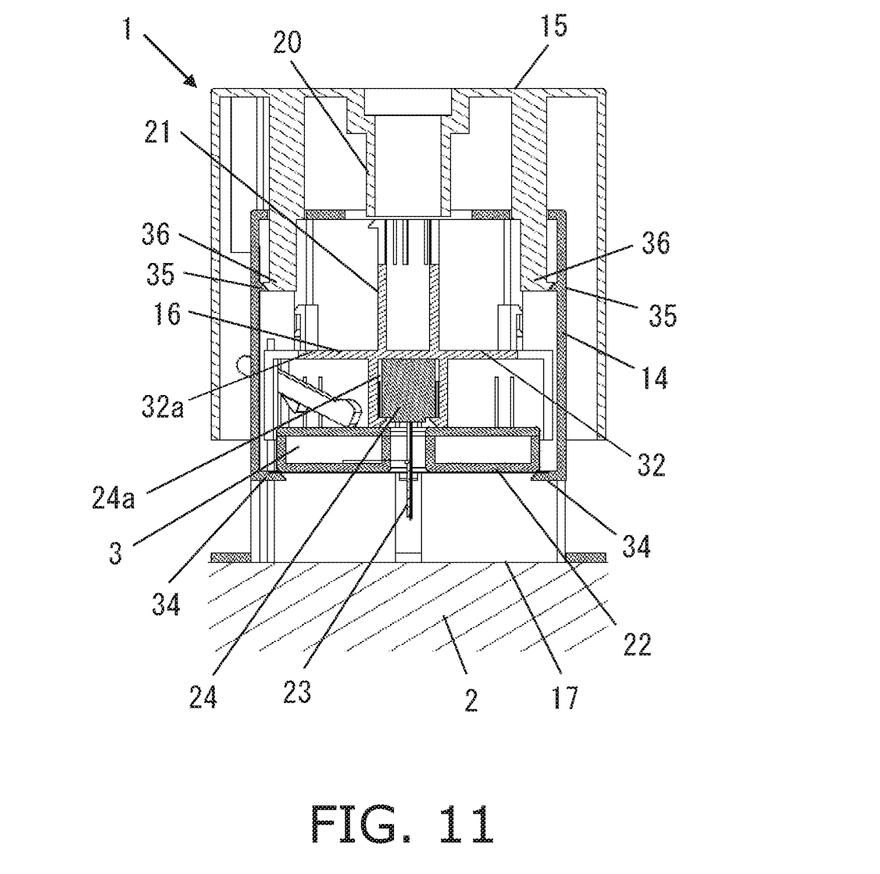
FIG. 11 is a cross section along the A-A line of the sensor insertion device in FIG. 8.
Figure 12:
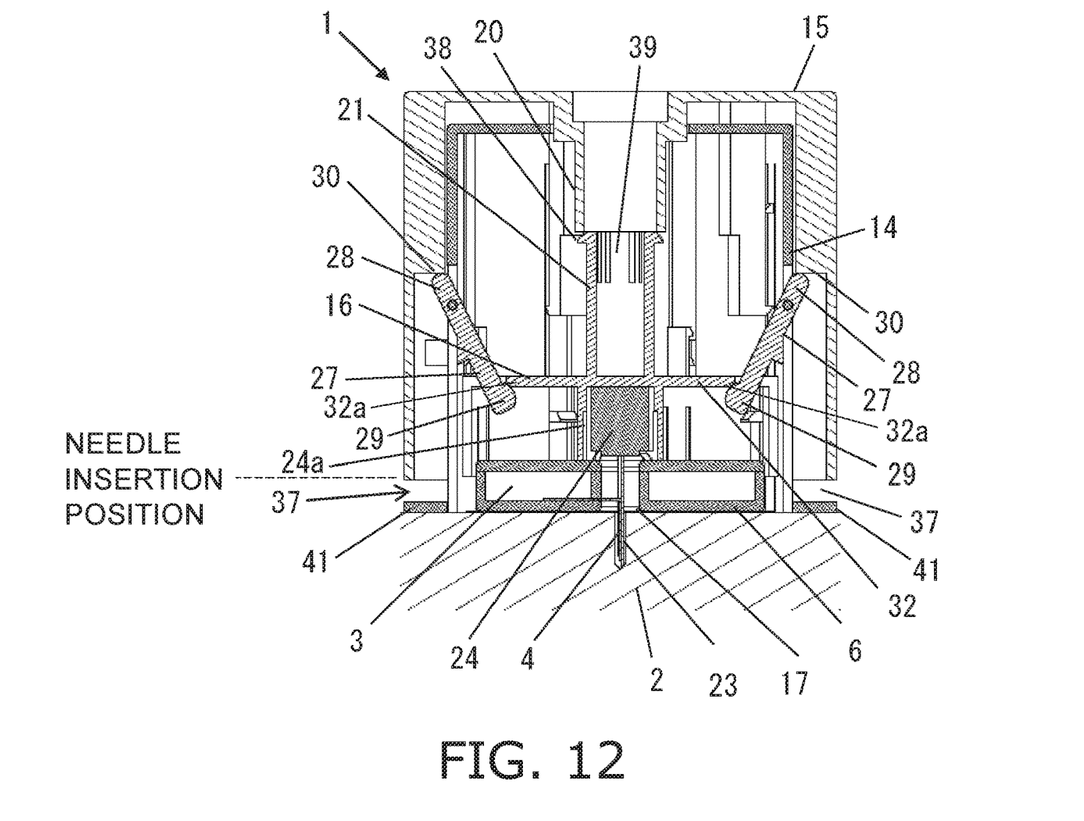
FIG. 12 is a cross section along the B-B line of the sensor insertion device in FIG. 8.

The carrier 16 has a cylindrical receiver 21 on its upper surface side. The operating body 20 (see FIG. 9) provided in the handle 15 abuts on the receiver 21. The lower end side of the carrier 16 is open, and the biological information measurement device 3 is detachably attached to a holder 22 provided inside the lower end side. Also, as shown in FIGS. 10 to 12, inside the lower end of the carrier 16, the guide needle unit 24, which includes the guide needle 23 to be inserted into the upper arm 2 of the patient, is attached to a guide needle unit holder 24a (an example of a guide needle holder).

Figure 13:
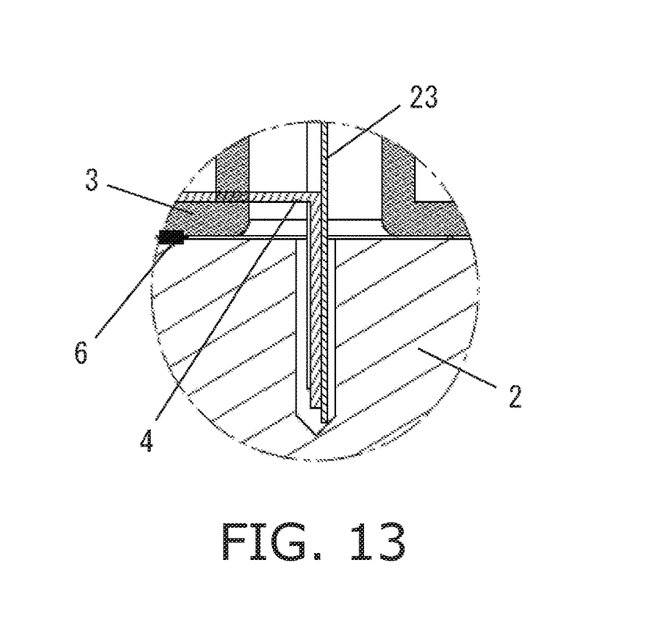
FIG. 13 is a detail view of the main part of the sensor insertion device in FIG. 12.

That is, the guide needle 23 is detachably held by the guide needle unit holder 24a. The guide needle 23 is made of metal and can move in and out of the lower end opening 17 of the sheath 14 in the needle insertion direction by sliding the carrier 16. As shown in FIG. 13, the guide needle 23 guides the sensor 4 in the insertion direction while holding the sensor 4, and inserts the sensor 4 into the upper arm 2 and leaves it there.

Figure 9:
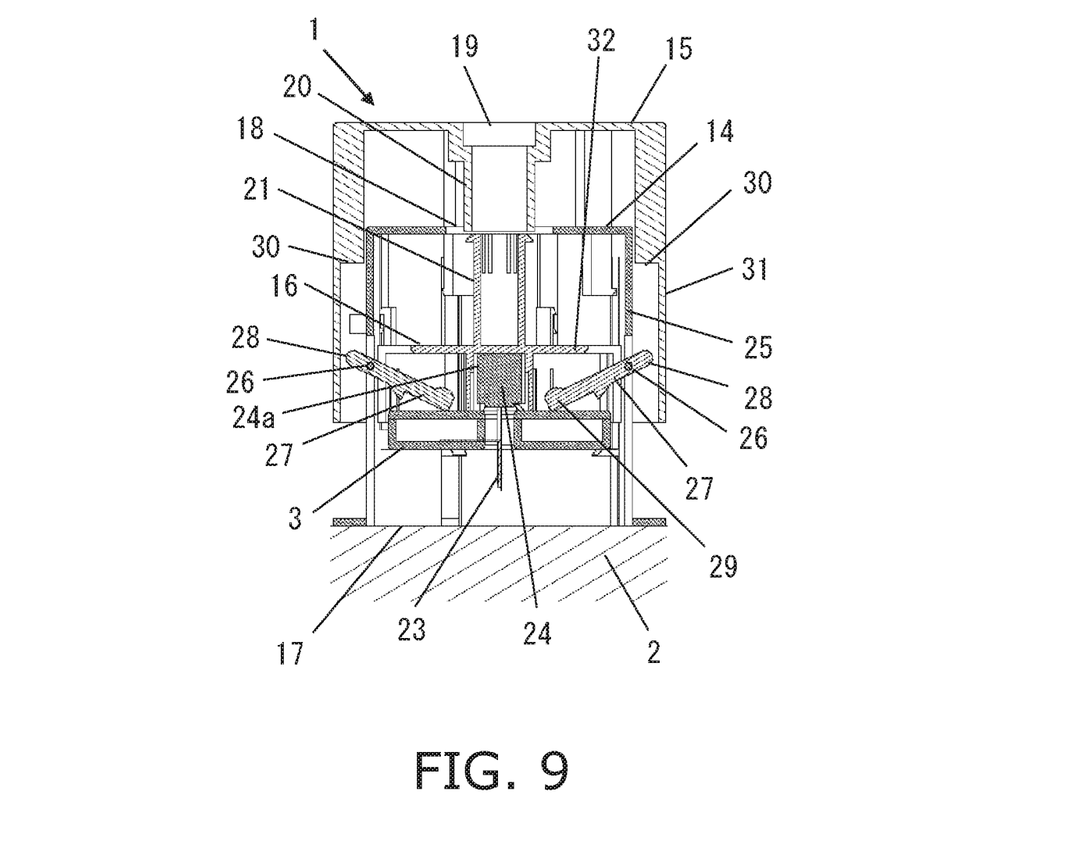
FIG. 9 is a cross section along the B-B line of the sensor insertion device in FIG. 8.

Then, as shown in FIG. 9, in the sheath 14, long arms 27 are rotatably supported by a rotation shaft 26 fixed to the cylindrical portion 25.

Figure 7:
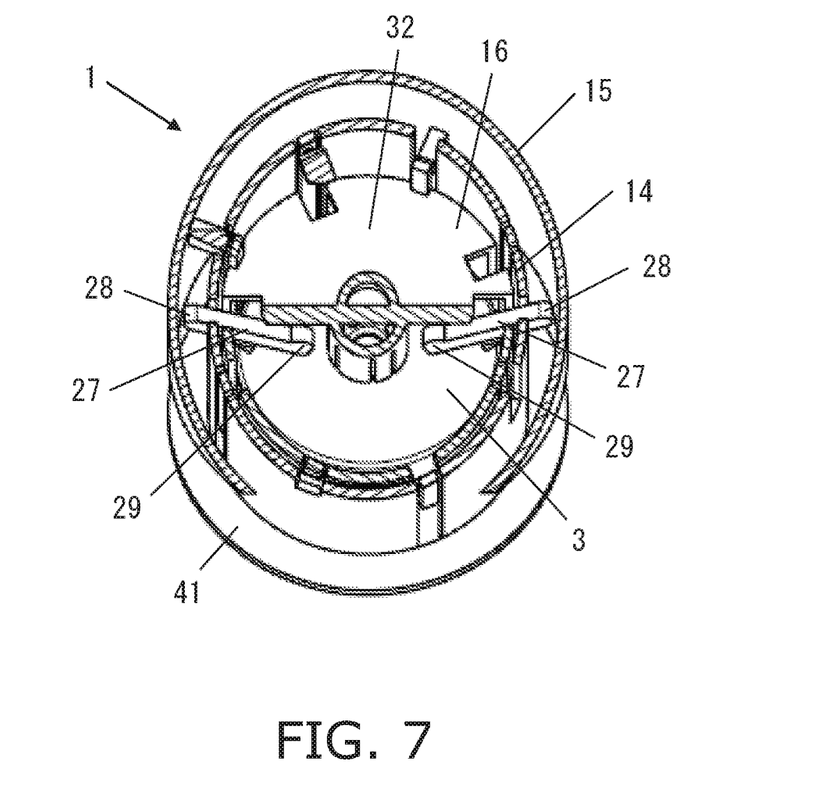
FIG. 7 is a cross sectional oblique view of the sensor insertion device in FIG. 5.

FIG. 7 is a cross section along the E-E line in FIG. 5. Two arms 27 are attached to the sheath 14 so as to be opposite each other at symmetrical positions in the sheath 14, and rotate around the rotation shaft 26 substantially in the radial direction of the cylindrical sheath 14. The arms 27 each have an outer end portion 28 disposed outside the sheath 14, and an inner end portion 29 disposed inside the sheath 14.

The arms 27 are such that the distance from the rotation shaft 26 to the outer end portion 28 is less than the distance from the rotation shaft 26 to the inner end portion 29.

Consequently, in a state in which no external force is being applied to the arms 27, the inner end portion 29 having a longer distance from the rotation shaft 26 is lowered and the outer end portion 28 is raised. Also, the inner end portion 29 side can be moved by a larger amount than the operation amount of the outer end portion 28 by operating the outer end portion 28 having a shorter distance from the rotation shaft 26.

The configuration and operation of rotating the arms 27 will be described below.

Figure 8:
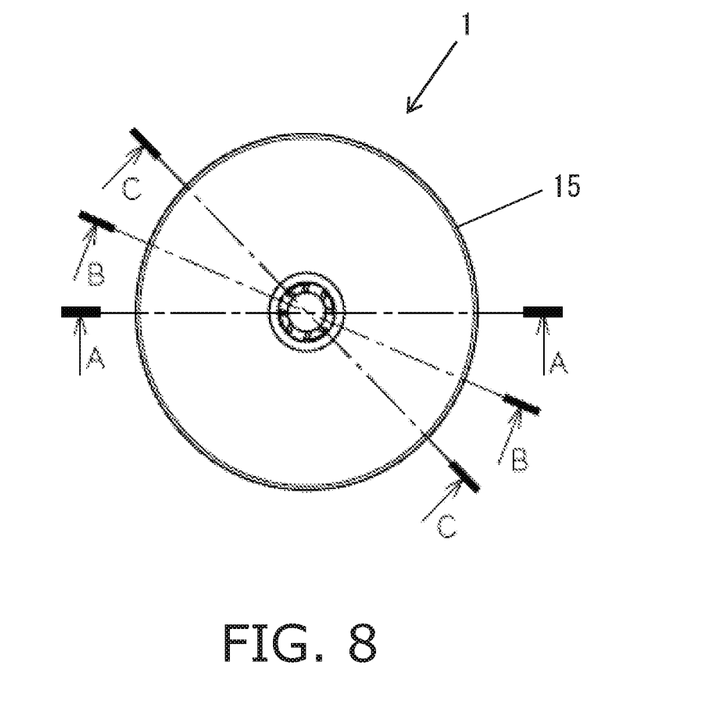
FIG. 8 is a top view of the sensor insertion device in FIG. 1.

FIG. 8 is a top view of the sensor insertion device 1, and FIG. 9 is a cross section along the B-B line in FIG. 8.

As shown in FIG. 9, an arm operation surface 30 that abuts on the outer end portions 28 of the arms 27 in the insertion direction of the sensor 4 is provided on the inner peripheral surface side of the handle 15. The arm operation surface 30 is a plane that is substantially perpendicular to the insertion direction of the sensor 4, and is provided between the cylindrical portion 31 of the handle 15 and the cylindrical portion 25 of the sheath 14.

The carrier 16 is provided with a ceiling 32 that abuts on the inner end portions 29 of the arms 27. The ceiling 32 is disposed so that its lower surface (an example of an arm receiver) 32a is opposite the inner end portions 29 of the arms. A guide needle unit 24 is attached to the guide needle unit holder 24a provided on the lower end side of the carrier 16. The guide needle 23 provided on the insertion side of the guide needle unit 24 projects downward, passing through the lower surface, from the central portion of the biological information measurement device 3 in the sensor insertion device 1.

FIG. 10 is a cross section along the C-C line in FIG. 8.

The outer peripheral portion of the biological information measurement device 3 is held by a holding rib 33 on the holder 22 provided on the inner peripheral surface side of the carrier 16. The inner end portions 29 of the arms 27 that have rotated downward are in contact with the upper surface of the biological information measurement device 3.

FIG. 11 is a cross section along the A-A line in FIG. 8.

The sheath 14 is such that a first holding piece 34, which is provided so as to project radially inward at the lower end portion, holds the biological information measurement device 3 and the carrier 16. Also, a second holding piece 35, which is provided so as to project radially inward above the first holding piece 34, holds the handle 15 via an operation protrusion 36 provided on the handle 15 side.

When the biological information measurement device 3 is attached to the upper arm 2 of the patient, the sensor inserting device 1 is used to insert and withdraw the guide needle 23.

In the insertion operation of the guide needle 23, the patient holds the handle 15 and brings the lower end opening 17 of the sensor insertion device 1 into contact with the patient's upper arm 2 as shown in FIG. 11.

From there, the patient pushes down on the handle 15. The handle 15 is held by the second holding piece 35 of the sheath 14 until at least a specific force is applied by the patient. Then, when the patient applies at least a specific force, the second holding piece 35 is expanded radially outward by the operation protrusion 36, and the sheath 14 releases its hold on the handle 15. Once released from being held, the handle 15 suddenly slides downward.

Also, when the second holding piece 35 of the sheath 14 is expanded radially outward, this causes the first holding piece 34 provided on the lower side also to expand radially outward. The biological information measurement device 3 and the carrier 16 are released from being held by the first holding piece 34, and slide downward.

Then, after the distal end of the guide needle 23 abuts on the upper arm 2, the receiver 21 of the carrier 16 is pushed downward by the operating body 20 and slides downward within the lower end opening portion 17, as shown in FIG. 12.

Then, the guide needle 23 is inserted at the insertion position shown in FIG. 12. At this point, in a state in which the arm operation surface 30 of the handle 15 is in contact with the outer end portions 28 of the arms 27, the guide needle 23 is pushed out of the lower end opening 17, and the distal end of the guide needle 23 projects from the lower end opening 17.

As a result, the guide needle 23 and the plastic sensor 4 that has been guided by the guide needle 23 are inserted into the patient's upper arm 2. That is, the guide needle 23 guides the sensor 4 in the insertion direction while holding the sensor 4, and inserts the sensor 4 into the upper arm 2 (see FIG. 13). The biological information measurement device 3 is affixed to the upper arm 2 via the adhesive portion 6.

From here, the guide needle 23 is withdrawn.

At the needle insertion position shown in FIG. 12, the inner end portions 29 of the arms 27 are in contact with the lower surface 32a side of the ceiling 32 of the carrier 16.

Figure 14:
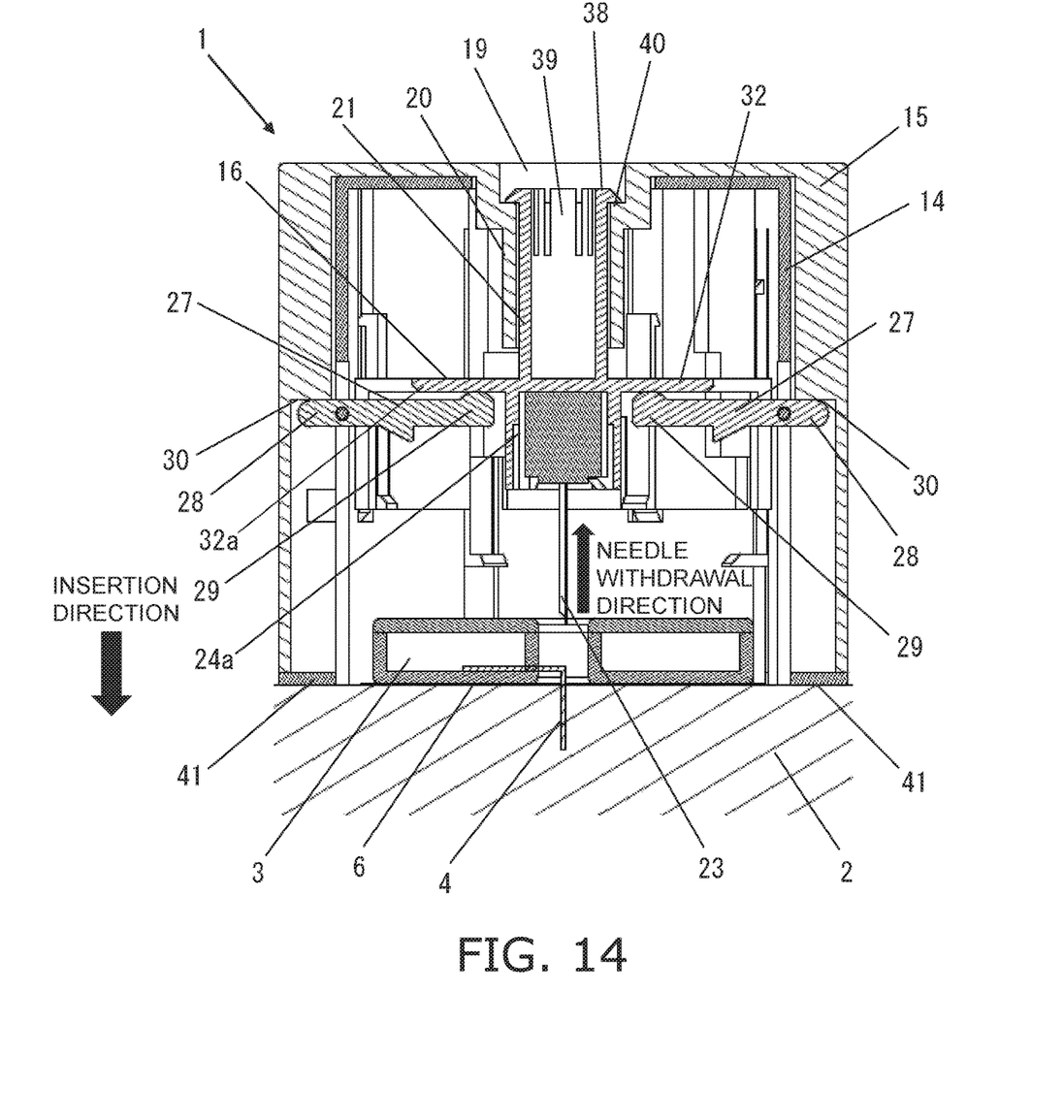
FIG. 14 is a cross section along the B-B line of the sensor insertion device in FIG. 8.

When the patient further pushes down the handle 15 from the needle insertion position shown in FIG. 12, the handle 15 slides downward. The arm operation surface 30 then pushes the outer end portions 28 of the arms 27 downward. As a result, the arms 27 rotate, and the inner end portions 29 of the arms 27 rotate upward as shown in FIG. 14.

At this point, as described above, the outer end portions 28 of the arms 27 are closer to the rotation shaft 26 than the inner end portions 29, so the inner end portions 29 can be rotated a distance that is greater than the distance the outer end portions 28 are rotated. Therefore, the inner end portion 29 side can be moved a large amount by just a small amount of operation on the outer end portion 28 side.

The inner end portions 29 abut on the lower surface 32a of the ceiling 32 of the carrier 16 and rotate further upward, so that the carrier 16 is pushed upward. Then, the guide needle 23, which moves integrally with the carrier 16, is pulled out of the upper arm 2 of the patient while the sensor 4 is left behind in the upper arm 2.

Consequently, the sensor 4 of the biological information measurement device 3 is in a state of being left in the upper arm 2, and the attachment of the biological information measurement device 3 is complete.

That is, in this embodiment, the arms 27 are rotated and the guide needle 23 is pulled out by an operation of further pushing down the handle 15 from the needle insertion position shown in FIG. 12.

Consequently, the guide needle 23 is pulled out without using a spring, so no snapping noise is produced by the release of the stored energy of the spring. As a result, the patient is subjected to less discomfort (fear).

With the sensor insertion device 1 in this embodiment, in order for the needle withdrawal operation of the guide needle 23 to be properly performed, as shown in FIG. 12, at the needle insertion position, a sliding space 37 for the handle 15 is formed between the lower end of the handle 15 and a flange portion 41.

Therefore, the handle 15 can be further pushed down from the needle insertion position, so the arm 27 can be rotated as described above.

As a result, the guide needle 23 can be withdrawn.

Also, in this embodiment, in order to perform the above-mentioned needle insertion operation and needle withdrawal operation, as shown in FIG. 12, an abutting protrusion 38 that projects outward is provided to the upper end portion of the receiver 21 of the carrier 16, at the portion that abuts on the operating body 20.

Therefore, during the needle insertion operation, the operating body 20 abuts on the abutting protrusion 38, and the carrier 16 can be slid downward.

As a result, the needle insertion operation can be carried out properly.

Also, for the needle withdrawal operation, as shown in FIG. 6, four bending portions 39 whose upper end side bends inward are provided at the upper end of the receiver 21. The abutting protrusion 38 is provided to the upper end of the bending portions 39. The receiver 21 is provided slidably inside the operating body 20.

Therefore, as shown in FIGS. 12 to 14, when the carrier 16 is pushed up in the needle withdrawal operation, the bending portions 39 of the receiver 21 bend inward in the radial direction, and the receiver 21 slides to the upper side (the opening 19 side) on the inner peripheral surface side of the operating body 20.

This allows the carrier 16 to be slid upward. As a result, the needle withdrawal operation can be carried out properly.

Furthermore, in this embodiment, as shown in FIG. 14, when the receiver 21 slides on the inner peripheral surface side of the operating body 20, a lock portion 40 that locks the receiver 21 is provided near the upper surface of the handle 15. More specifically, the lock portion 40 is provided at the opening 19 of the handle 15, and is engaged with the abutting protrusion 38 provided on the upper end portion of the carrier 16.

Therefore, the carrier 16 is coupled to the handle 15 by the engagement between the abutting protrusion 38 and the lock portion 40 when the needle withdrawal operation is performed.

As a result, the carrier 16 is held by the handle 15 in a state in which the guide needle 23 has been withdrawn.

As described above, when the needle withdrawal operation is performed by rotation of the arms 27, the needle withdrawal operation is performed very quietly, and this may make it difficult to tell that attachment of the biological information measurement device 3 is complete.

In view of this, with the sensor insertion device 1 of this embodiment, as shown in FIGS. 12 and 14, the flange portion 41, which protrudes outward from the outer surface, is provided at the lower end of the sheath 14. The flange portion 41 is in contact with the lower end of the handle 15.

Therefore, when the handle 15 is pushed all the way down in the needle withdrawal operation, the lower end of the handle 15 comes into contact with the flange portion 41. At this point, due contact between the two pieces of plastic produces a small impact noise between them. This small impact noise between the plastic pieces tells the patient that attachment is complete.

Also, the flat part of the flange portion 41 hits the upper arm 2 and makes stable surface contact, thereby stabilizing the orientation of the sensor insertion device 1. As a result, it is possible to reliably produce an impact noise between the plastic pieces.

Furthermore, since the flange portion 41 is in surface contact with the upper arm 2 on the lower surface side, it does not dig into the upper arm 2 as much. Therefore, at the lower end opening 17, the upper arm 2 surrounded by the lower end opening 17 does not bulge up into the sheath 14 as much, and the upper arm 2 surrounded by the lower end opening 17 is stabilized. As a result, the biological information measurement device 3 is attached to the stable upper arm 2.

INDUSTRIAL APPLICABILITY

The present invention is anticipated to find use as a sensor insertion device for inserting into a patient's body a sensor that measures biological information in order to perform continuous blood glucose measurement, for example.

REFERENCE SIGNS LIST 1 sensor insertion device (sensor insertion device)
2 upper arm
3 biological information measurement device
4 sensor
5 subcutaneous tissue
6 adhesive part
7 measurement unit
8 controller
9 battery
10 temperature sensor
11 memory unit
12 communication unit
13 mobile phone
14 sheath
15 handle
16 carrier
17 lower end opening
18 upper end opening
19 opening
20 operating body
21 receiver
22 holder
23 guide needle
24 guide needle unit
24a guide needle unit holder (guide needle holder)
25 cylindrical portion
26 shaft
27 arm
28 outer end portion
29 inner end portion
30 arm operation surface
31 cylindrical portion
32 ceiling
32a lower surface (arm receiver)
33 holding rib
34 first holding piece
35 second holding piece
36 operation protrusion
37 sliding space
38 abutting protrusion
39 bending portion
40 lock portion
41 flange portion

The invention claimed is:

1. A sensor insertion device for inserting into a patient's body a sensor for measuring biological information, the sensor insertion device comprising:
   a cylindrical sheath having a lower end opening and an upper end opening;
   a cylindrical handle configured to slidably cover an outer peripheral surface of the cylindrical sheath and to slide up and down in an axial direction of the cylindrical sheath;

an operating body that is provided in the cylindrical handle and configured to move up and down integrally with the cylindrical handle;

a carrier that is provided below the operating body;

a guide needle holder that is provided at a lower end of the carrier, and configured to detachably hold a guide needle that is inserted into the patient's body at a specific insertion position for guiding the sensor in an insertion direction; and an arm that is supported rotatably around a rotation shaft fixed to the cylindrical sheath, the arm including an outer end portion disposed on an outer peripheral surface side of the cylindrical sheath, and an inner end portion disposed on an inner peripheral surface side of the cylindrical sheath, the cylindrical handle including an arm operation surface that abuts on the outer end portion of the arm, the carrier including an arm receiver that abuts on the inner end portion of the arm, the operating body formed in a cylindrical shape, the carrier further including a cylindrical receiver that abuts on the operating body, the cylindrical receiver including a bending portion bending inward, the bending portion including an abutting protrusion that abuts on the operating body, the cylindrical receiver slidably provided inside the operating body, and the cylindrical handle including a lock portion configured to lock the cylindrical receiver when the cylindrical receiver has slid inside the operating body.

2. The sensor insertion device according to claim 1, wherein, when the cylindrical handle is pushed down in the insertion direction, the guide needle is configured to be inserted into the patient's body at the specific insertion position.

3. The sensor insertion device according to claim 2, wherein, when the cylindrical handle is further pushed down from the specific insertion position in the insertion direction, the arm operation surface of the cylindrical handle abuts on the outer end portion of the arm and the arm rotates around the rotation shaft, and the inner end portion of the arm abuts on the arm receiver of the carrier and moves the carrier together with the guide needle to an opposite side from the insertion direction.

4. The sensor insertion device according to claim 1, wherein at least two of the arms are provided.

5. The sensor insertion device according to claim 4, wherein the arms are provided at symmetrical positions on the cylindrical sheath.

6. The sensor insertion device according to claim 1, wherein the cylindrical sheath has a substantially cylindrical shape, and the arm rotates substantially in a radial direction of the cylindrical sheath.

7. The sensor insertion device according to claim 1, wherein the arm is disposed such that a distance from the rotation shaft to the inner end portion is greater than a distance from the rotation shaft to the outer end portion.

8. The sensor insertion device according to claim 1, wherein the arm operation surface is provided between a cylindrical portion of the cylindrical handle and a cylindrical portion of the cylindrical sheath.

9. The sensor insertion device according to claim 1, wherein a lower end of the guide needle is disposed lower than the lower end opening in a state in which the arm operation surface is in contact with the outer end portion of the arm.

10. The sensor insertion device according to claim 9, wherein a sliding space for the cylindrical handle is provided below a lower end of the cylindrical handle, in a state in which the arm operation surface is in contact with the outer end portion of the arm near the specific insertion position.

11. The sensor insertion device according to claim 1, wherein the cylindrical sheath further has a flange portion provided at a lower end of the cylindrical sheath, and the flange portion abuts on a lower end of the cylindrical handle.

* * * * *